US008216267B2

(12) United States Patent
Pallazza

(10) Patent No.: US 8,216,267 B2
(45) Date of Patent: Jul. 10, 2012

(54) MULTILAYER BALLOON FOR BIFURCATED STENT DELIVERY AND METHODS OF MAKING AND USING THE SAME

(75) Inventor: Stefan M. Pallazza, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 693 days.

(21) Appl. No.: 11/519,420

(22) Filed: Sep. 12, 2006

(65) Prior Publication Data

US 2008/0065188 A1 Mar. 13, 2008

(51) Int. Cl.
*A61F 2/06* (2006.01)
*A61M 29/00* (2006.01)

(52) U.S. Cl. ....... 606/194; 606/191; 606/192; 623/1.35; 623/1.11; 604/101.02

(58) Field of Classification Search ................. 623/1.11, 623/1.15, 1.35; 606/108, 191–192, 194; 604/96.01–103.14; 600/207
See application file for complete search history.

(56) References Cited

U.S. PATENT DOCUMENTS

| 4,309,994 | A | 1/1982 | Grunwald | 128/214 R |
|---|---|---|---|---|
| 4,490,421 | A | 12/1984 | Levy | 428/35 |
| 4,769,005 | A | 9/1988 | Ginsburg et al. | 604/53 |
| 4,774,949 | A | 10/1988 | Fogarty | 128/348.1 |
| 4,896,670 | A | 1/1990 | Crittenden | 606/194 |
| 4,905,667 | A | 3/1990 | Foerster et al. | 128/4 |
| 4,994,071 | A | 2/1991 | MacGregor | 606/194 |
| 5,116,318 | A * | 5/1992 | Hillstead | 604/103.14 |
| 5,342,387 | A | 8/1994 | Summers | 606/198 |
| 5,348,538 | A | 9/1994 | Wang et al. | 604/96 |
| 5,385,776 | A | 1/1995 | Maxfield et al. | 428/297 |
| 5,387,235 | A | 2/1995 | Chuter | 623/1 |
| 5,403,340 | A | 4/1995 | Wang et al. | 606/194 |
| 5,447,497 | A | 9/1995 | Sogard et al. | 604/101 |
| 5,456,712 | A | 10/1995 | Maginot | 623/1 |
| 5,476,471 | A | 12/1995 | Shifrin et al. | 606/151 |
| 5,487,730 | A | 1/1996 | Marcadis et al. | 604/96 |
| 5,500,181 | A | 3/1996 | Wang et al. | 264/532 |
| 5,556,383 | A | 9/1996 | Wang et al. | 604/96 |
| 5,591,228 | A | 1/1997 | Edoga | 623/1 |
| 5,607,444 | A | 3/1997 | Lam | 606/194 |
| 5,609,605 | A | 3/1997 | Marshall et al. | 606/191 |

(Continued)

FOREIGN PATENT DOCUMENTS

CA 2220864 7/1999

(Continued)

OTHER PUBLICATIONS

U.S. Appl. No. 09/325,996, filed Jun. 4, 1999, Vardi et al.

(Continued)

*Primary Examiner* — Corrine M McDermott
*Assistant Examiner* — Mark Mashack
(74) *Attorney, Agent, or Firm* — Vidas, Arrett & Steinkraus, P.A.

(57) ABSTRACT

An expandable medical balloon useful for treatment at a vessel bifurcation, the balloon having at least one expanded state, the balloon having at least one inner layer and at least one outer layer, the outer layer having at least one cavity therein through which the inner layer protrudes when the balloon is in its at least one expanded state, and methods of making and using the same.

8 Claims, 13 Drawing Sheets

U.S. PATENT DOCUMENTS

| | | | |
|---|---|---|---|
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |
| 5,632,772 A | 5/1997 | Alcime et al. | 623/1 |
| 5,636,641 A | 6/1997 | Fariabi | 600/585 |
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |
| 5,697,971 A | 12/1997 | Fischell et al. | 623/1 |
| 5,707,348 A | 1/1998 | Krogh | 602/41 |
| 5,709,713 A | 1/1998 | Evans et al. | 623/1 |
| 5,714,110 A | 2/1998 | Wang et al. | 264/529 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,755,773 A | 5/1998 | Evans et al. | 623/1 |
| 5,755,778 A | 5/1998 | Kleshinski | 623/1 |
| 5,782,906 A | 7/1998 | Marshall et al. | 623/1 |
| 5,824,036 A | 10/1998 | Lauterjung | 623/1 |
| 5,824,040 A | 10/1998 | Cox et al. | 623/1 |
| 5,826,588 A | 10/1998 | Forman | 128/898 |
| 5,827,320 A | 10/1998 | Richter et al. | 606/194 |
| 5,830,182 A | 11/1998 | Wang et al. | 604/96 |
| 5,843,116 A * | 12/1998 | Crocker et al. | 606/192 |
| 5,851,464 A | 12/1998 | Davila et al. | 264/103 |
| 5,868,777 A | 2/1999 | Lam | 606/194 |
| 5,893,887 A | 4/1999 | Jayaraman | 623/1 |
| 5,951,941 A | 9/1999 | Wang et al. | 264/523 |
| 5,961,548 A | 10/1999 | Shmulewitz | 623/1 |
| 5,972,017 A | 10/1999 | Berg et al. | 606/198 |
| 6,013,054 A | 1/2000 | Jiun Yan | 604/96 |
| 6,017,324 A | 1/2000 | Tu et al. | 604/96 |
| 6,017,363 A | 1/2000 | Hojeibane | 623/1 |
| 6,024,722 A | 2/2000 | Rau et al. | 604/96 |
| 6,030,414 A | 2/2000 | Taheri | 623/1 |
| 6,033,434 A | 3/2000 | Borghi | 623/1 |
| 6,033,435 A | 3/2000 | Penn et al. | 623/1 |
| 6,056,775 A | 5/2000 | Borghi et al. | 623/1.16 |
| 6,059,824 A | 5/2000 | Taheri | 623/1 |
| 6,068,655 A | 5/2000 | Seguin et al. | 623/1 |
| 6,086,611 A | 7/2000 | Duffy et al. | 623/1 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,124,007 A * | 9/2000 | Wang et al. | 428/35.2 |
| 6,129,738 A | 10/2000 | Lashinski et al. | 606/194 |
| 6,142,973 A | 11/2000 | Carleton et al. | 604/96 |
| 6,143,002 A | 11/2000 | Vietmeier | 606/108 |
| 6,146,356 A | 11/2000 | Wang et al. | 604/96 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,171,278 B1 | 1/2001 | Wang et al. | 604/96 |
| 6,183,509 B1 | 2/2001 | Dibie | 623/1.35 |
| 6,203,568 B1 | 3/2001 | Lombardi et al. | 623/1.13 |
| 6,210,380 B1 | 4/2001 | Mauch | 604/284 |
| 6,210,429 B1 | 4/2001 | Vardi et al. | 623/1.11 |
| 6,210,433 B1 | 4/2001 | Larre | 623/1.15 |
| 6,251,980 B1 | 6/2001 | Lan et al. | 524/445 |
| 6,254,593 B1 | 7/2001 | Wilson | 606/1.11 |
| 6,258,115 B1 | 7/2001 | Dubrul | 606/200 |
| 6,258,116 B1 | 7/2001 | Hojeibane | 623/1.16 |
| 6,261,305 B1 * | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,290,673 B1 | 9/2001 | Shanley | 604/102.02 |
| 6,293,968 B1 | 9/2001 | Taheri | 623/1.15 |
| 6,325,826 B1 | 12/2001 | Vardi et al. | 623/1.35 |
| 6,334,864 B1 | 1/2002 | Amplatz et al. | 606/200 |
| 6,346,089 B1 | 2/2002 | Dibie | 603/1.15 |
| 6,355,060 B1 | 3/2002 | Lenker et al. | 623/1.34 |
| 6,361,544 B1 | 3/2002 | Wilson et al. | 606/194 |
| 6,361,555 B1 | 3/2002 | Wilson | 623/1.11 |
| 6,383,213 B2 | 5/2002 | Wilson et al. | 623/1.11 |
| 6,395,018 B1 | 5/2002 | Castaneda | 623/1.13 |
| 6,436,104 B2 | 8/2002 | Hojeibane | 606/108 |
| 6,436,134 B2 | 8/2002 | Richter et al. | 623/1.15 |
| 6,508,836 B2 | 1/2003 | Wilson et al. | 623/1.35 |
| 6,517,558 B2 | 2/2003 | Gittings et al. | 606/153 |
| 6,520,988 B1 | 2/2003 | Colombo et al. | 623/1.35 |
| 6,540,779 B2 | 4/2003 | Richter et al. | 623/1.35 |
| 6,579,309 B1 | 6/2003 | Loos et al. | 623/1.16 |
| 6,579,312 B2 | 6/2003 | Wilson et al. | 623/1.35 |
| 6,582,394 B1 | 6/2003 | Reiss et al. | 604/96.01 |
| 6,596,020 B2 | 7/2003 | Vardi et al. | 623/1.11 |
| 6,599,316 B2 | 7/2003 | Vardi et al. | 623/1.15 |
| 6,645,242 B1 | 11/2003 | Quinn | 623/1.16 |
| 6,689,156 B1 | 2/2004 | Davidson et al. | 623/1.11 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,749,628 B1 | 6/2004 | Callol et al. | 623/1.15 |
| 6,776,793 B2 | 8/2004 | Brown et al. | 623/1.15 |
| 6,811,566 B1 | 11/2004 | Penn et al. | 623/1.15 |
| 6,835,203 B1 | 12/2004 | Vardi et al. | 623/1.34 |
| 6,858,038 B2 | 2/2005 | Heuser | 623/1.35 |
| 6,884,258 B2 | 4/2005 | Vardi et al. | 623/1.11 |
| 6,896,699 B2 | 5/2005 | Wilson et al. | 623/1.35 |
| 6,932,837 B2 | 8/2005 | Amplatz et al. | 623/1.15 |
| 6,955,687 B2 | 10/2005 | Richter et al. | 623/1.35 |
| 6,955,688 B2 | 10/2005 | Wilson et al. | 623/1.35 |
| 6,962,602 B2 | 11/2005 | Vardi et al. | 623/1.11 |
| 7,018,400 B2 | 3/2006 | Lashinski et al. | 623/1.11 |
| 7,056,323 B2 | 6/2006 | Mareiro et al. | 606/108 |
| 7,060,091 B2 | 6/2006 | Killion et al. | 623/1.15 |
| 7,776,079 B2 * | 8/2010 | Gumm | 623/1.11 |
| 7,799,064 B2 * | 9/2010 | Brucker et al. | 623/1.11 |
| 2001/0003161 A1 | 6/2001 | Vardi et al. | 623/1.11 |
| 2001/0004706 A1 | 6/2001 | Hojeibane | 623/1.11 |
| 2001/0004707 A1 | 6/2001 | Dereurne et al. | 623/1.16 |
| 2001/0012927 A1 | 8/2001 | Mauch | 604/284 |
| 2001/0016766 A1 | 8/2001 | Vardi et al. | 623/1.11 |
| 2001/0016767 A1 | 8/2001 | Wilson et al. | 623/1.11 |
| 2001/0016768 A1 | 8/2001 | Wilson et al. | 623/1.11 |
| 2001/0025195 A1 | 9/2001 | Shaolian et al. | 623/1.13 |
| 2001/0027291 A1 | 10/2001 | Shanley | 604/104 |
| 2001/0027338 A1 | 10/2001 | Greenberg | 623/1.13 |
| 2001/0029396 A1 | 10/2001 | Wilson et al. | 623/1.11 |
| 2001/0037116 A1 | 11/2001 | Wilson et al. | 606/108 |
| 2001/0037138 A1 | 11/2001 | Wilson et al. | 623/1.11 |
| 2001/0039448 A1 | 11/2001 | Dibie | 623/1.16 |
| 2001/0049552 A1 | 12/2001 | Richter et al. | 623/1.15 |
| 2001/0056297 A1 | 12/2001 | Hojeibane | 623/1.16 |
| 2002/0013618 A1 | 1/2002 | Marotta et al. | 623/1.15 |
| 2002/0013619 A1 | 1/2002 | Shanley | 623/1.15 |
| 2002/0022874 A1 | 2/2002 | Wilson | 623/1.11 |
| 2002/0026232 A1 | 2/2002 | Marotta et al. | 623/1.16 |
| 2002/0035392 A1 | 3/2002 | Wilson | 623/1.11 |
| 2002/0042650 A1 | 4/2002 | Vardi et al. | 623/1.35 |
| 2002/0052648 A1 | 5/2002 | McGuckin, Jr. et al. | 623/1.35 |
| 2002/0072790 A1 | 6/2002 | McGuckin, Jr. et al. | 623/1.12 |
| 2002/0111675 A1 | 8/2002 | Wilson | 623/1.35 |
| 2002/0156516 A1 | 10/2002 | Vardi et al. | 623/1.11 |
| 2002/0156517 A1 | 10/2002 | Perouse | 623/1.11 |
| 2002/0165604 A1 | 11/2002 | Shanley | 623/1.15 |
| 2002/0173835 A1 | 11/2002 | Bourang et al. | 623/1.11 |
| 2002/0173840 A1 | 11/2002 | Brucker et al. | 623/1.16 |
| 2002/0183763 A1 | 12/2002 | Callol et al. | 606/108 |
| 2002/0183780 A1 * | 12/2002 | Wang | 606/194 |
| 2002/0193872 A1 | 12/2002 | Trout, III et al. | 623/1.34 |
| 2002/0193873 A1 | 12/2002 | Brucker et al. | 623/1.35 |
| 2003/0009209 A1 | 1/2003 | Hojeibane | 623/1.11 |
| 2003/0028233 A1 | 2/2003 | Vardi et al. | 623/1.11 |
| 2003/0050688 A1 | 3/2003 | Fischell et al. | 623/1.15 |
| 2003/0055378 A1 | 3/2003 | Wang et al. | 604/103.07 |
| 2003/0055483 A1 | 3/2003 | Gumm | 623/1.11 |
| 2003/0074047 A1 | 4/2003 | Richter | 623/1.11 |

| Publication No. | Date | Inventor | Class |
|---|---|---|---|
| 2003/0093109 A1 | 5/2003 | Mauch | 606/194 |
| 2003/0097169 A1 | 5/2003 | Brucker | 623/1.11 |
| 2003/0114912 A1 | 6/2003 | Sequin et al. | 623/1.11 |
| 2003/0125791 A1 | 7/2003 | Sequin et al. | 623/1.11 |
| 2003/0125802 A1 | 7/2003 | Callol et al. | 623/1.35 |
| 2003/0130716 A1* | 7/2003 | Weber et al. | 623/1.11 |
| 2003/0135259 A1 | 7/2003 | Simso | 623/1.12 |
| 2003/0181923 A1 | 9/2003 | Vardi | 606/108 |
| 2003/0195606 A1 | 10/2003 | Davidson et al. | 623/1.11 |
| 2004/0006381 A1 | 1/2004 | Sequin et al. | 623/1.12 |
| 2004/0015227 A1 | 1/2004 | Vardi et al. | 623/1.16 |
| 2004/0044396 A1 | 3/2004 | Clerc et al. | 623/1.13 |
| 2004/0059406 A1 | 3/2004 | Cully et al. | 623/1.11 |
| 2004/0088007 A1 | 5/2004 | Eidenschink | 607/1 |
| 2004/0117003 A1 | 6/2004 | Ouriel et al. | 623/1.35 |
| 2004/0133268 A1 | 7/2004 | Davidson et al. | 623/1.35 |
| 2004/0138732 A1 | 7/2004 | Suhr et al. | 623/1.11 |
| 2004/0138737 A1 | 7/2004 | Davidson et al. | 623/1.35 |
| 2004/0148006 A1 | 7/2004 | Davidson et al. | 623/1.11 |
| 2004/0172121 A1 | 9/2004 | Eidenschink et al. | 623/1.11 |
| 2004/0186560 A1 | 9/2004 | Alt | 623/1.35 |
| 2004/0225345 A1 | 11/2004 | Fischell et al. | 623/1.11 |
| 2004/0267352 A1 | 12/2004 | Davidson et al. | 623/1.15 |
| 2005/0004656 A1 | 1/2005 | Das | 623/1.16 |
| 2005/0010278 A1 | 1/2005 | Vardi et al. | 623/1.35 |
| 2005/0015108 A1 | 1/2005 | Williams et al. | 606/194 |
| 2005/0015135 A1 | 1/2005 | Shanley | 623/1.11 |
| 2005/0060027 A1 | 3/2005 | Khenansho et al. | 623/1.35 |
| 2005/0096726 A1 | 5/2005 | Sequin et al. | 623/1.12 |
| 2005/0102021 A1 | 5/2005 | Osborne | 623/1.13 |
| 2005/0102023 A1 | 5/2005 | Yadin et al. | 623/1.15 |
| 2005/0119731 A1 | 6/2005 | Brucker et al. | 623/1.35 |
| 2005/0125076 A1 | 6/2005 | Ginn | 623/23.65 |
| 2005/0131526 A1 | 6/2005 | Wong | 623/1.11 |
| 2005/0149161 A1 | 7/2005 | Eidenschink et al. | 623/1.11 |
| 2005/0149177 A1 | 7/2005 | Weber et al. | 623/1.46 |
| 2005/0154442 A1 | 7/2005 | Eidenschink et al. | 623/1.11 |
| 2005/0154444 A1 | 7/2005 | Quadri | 623/1.13 |
| 2005/0183728 A1 | 8/2005 | Eidenschink et al. | 29/508 |
| 2005/0209673 A1 | 9/2005 | Shaked | 623/1.11 |
| 2005/0222668 A1 | 10/2005 | Schaeffer et al. | |
| 2005/0228483 A1 | 10/2005 | Kaplan et al. | 623/1.15 |
| 2005/0273149 A1* | 12/2005 | Tran et al. | 623/1.11 |
| 2006/0036315 A1 | 2/2006 | Yadin et al. | 623/1.35 |
| 2006/0041303 A1 | 2/2006 | Israel | 623/1.11 |
| 2006/0074476 A1* | 4/2006 | Holman et al. | 623/1.11 |
| 2006/0079956 A1 | 4/2006 | Eigler et al. | 623/1.35 |
| 2006/0173528 A1 | 8/2006 | Feld et al. | 623/1.15 |
| 2007/0073376 A1 | 3/2007 | Krolik et al. | 623/1.11 |
| 2008/0208307 A1* | 8/2008 | Ben-Muvhar et al. | 623/1.11 |

FOREIGN PATENT DOCUMENTS

| | | |
|---|---|---|
| DE | 9014845 | 2/1991 |
| DE | 29701758 | 3/1997 |
| DE | 29701883 | 5/1997 |
| EP | 0479730 | 10/1991 |
| EP | 0751752 | 1/1997 |
| EP | 0 768 097 | 4/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | WO 93/04118 | 3/1993 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/36709 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15109 | 4/1999 |
| WO | 99/24104 | 5/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 01/45594 | 6/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 00/74595 | 12/2000 |
| WO | 01/21095 | 3/2001 |
| WO | 01/21109 | 3/2001 |
| WO | 01/21244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | WO03/049795 A2 | 6/2003 |
| WO | 03/055414 | 7/2003 |
| WO | 03/063924 | 8/2003 |

| WO | 2004/026174 | | 4/2004 |
| WO | 2004/026180 | | 4/2004 |
| WO | 2005/009295 | | 2/2005 |
| WO | 2005/014077 | | 2/2005 |
| WO | 2005041810 | | 5/2005 |
| WO | WO 2005/041810 | * | 5/2005 |
| WO | 2006/028925 | | 3/2006 |
| WO | 2006074476 | | 7/2006 |

OTHER PUBLICATIONS

U.S. Appl. No. 09/614,472, filed Jul. 11, 2000, Davidson et al.

U.S. Appl. No. 09/663,111, filed Sep. 15, 2000, Davidson et al.

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

Caputo, Ronald P., "Stent Jail: A Minimum-Security Prison," *The American Journal of Cardiology*, vol. 77, pp. 1226-1230 (Jun. 1, 1996).

Colombo, M.D., Antonio, ""Kissing" Stent for Bifurcational Coronary Lesion," *Catheterization and Cardiovascular Diagnosis*, vol. 30, pp. 327-330 (Dec. 1993).

Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: To Treat or Not to Treat," *Catheterization and Cardiovascular Interventions*, vol. 50, pp. 411-412 (2000).

* cited by examiner

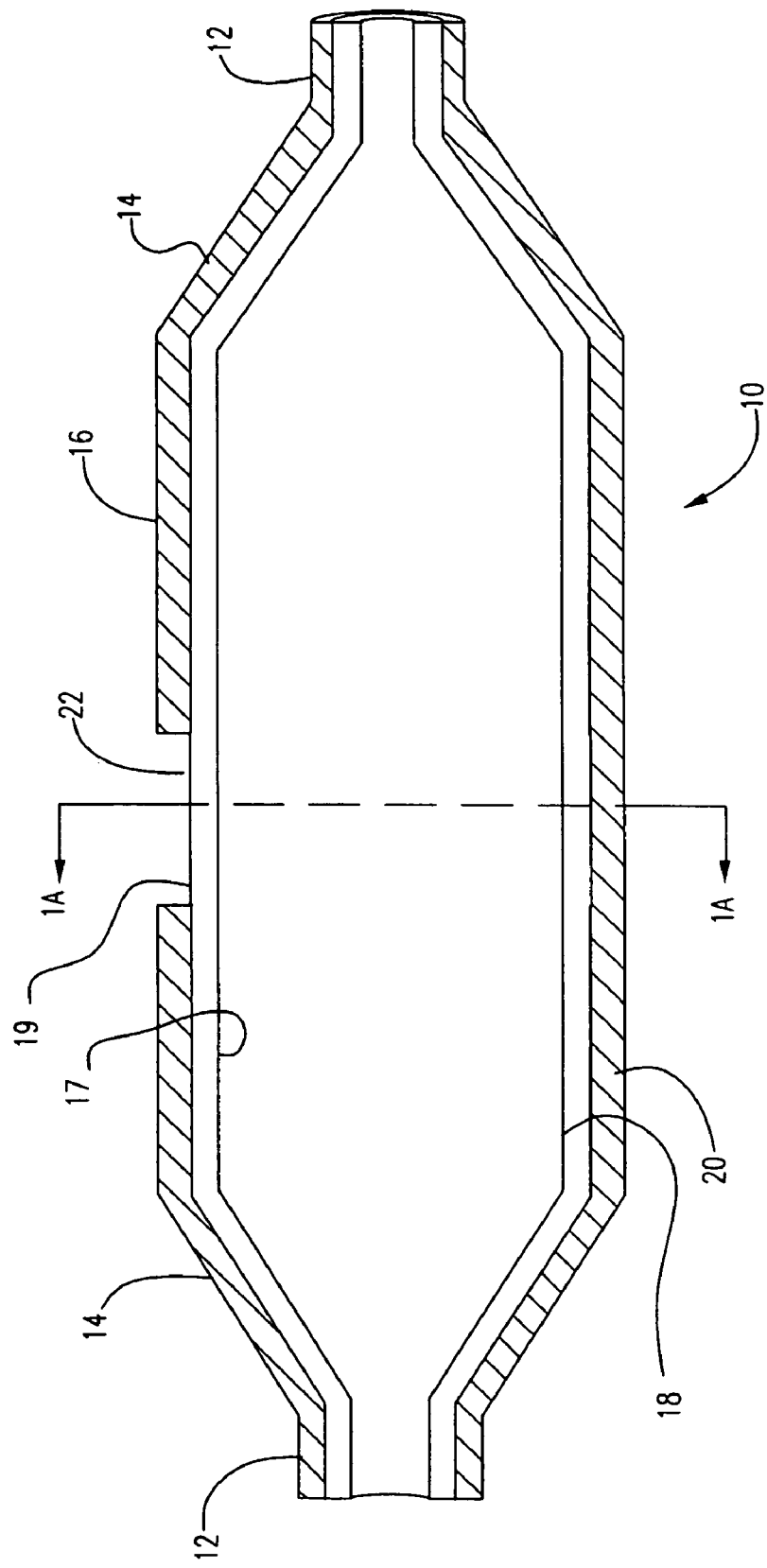

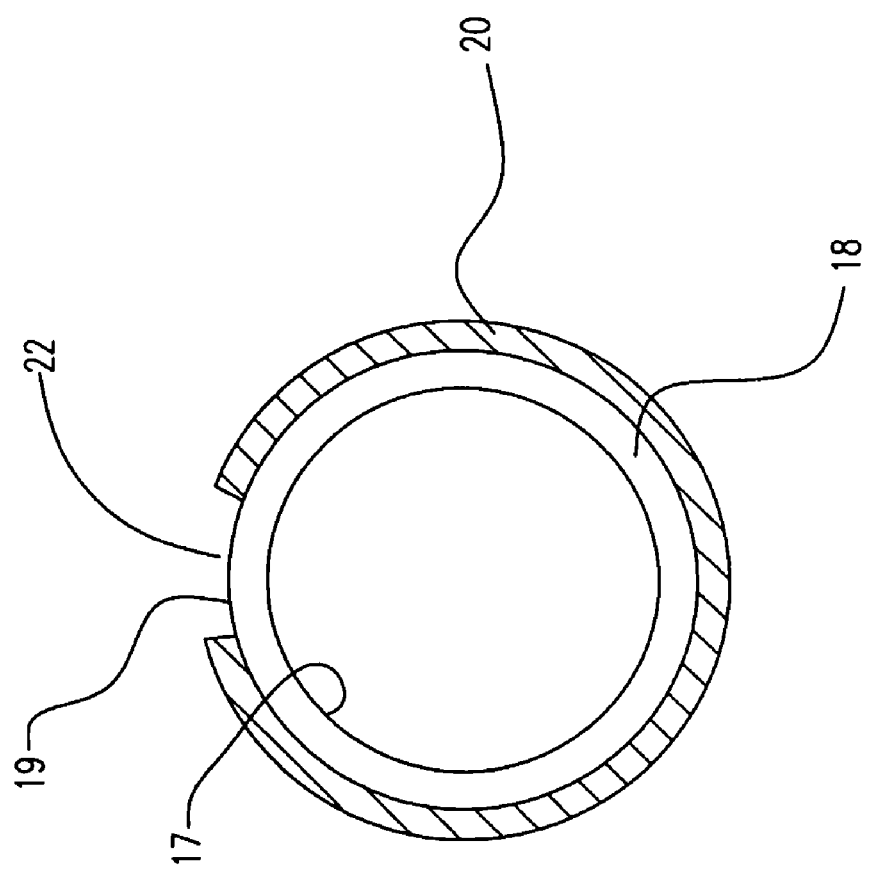

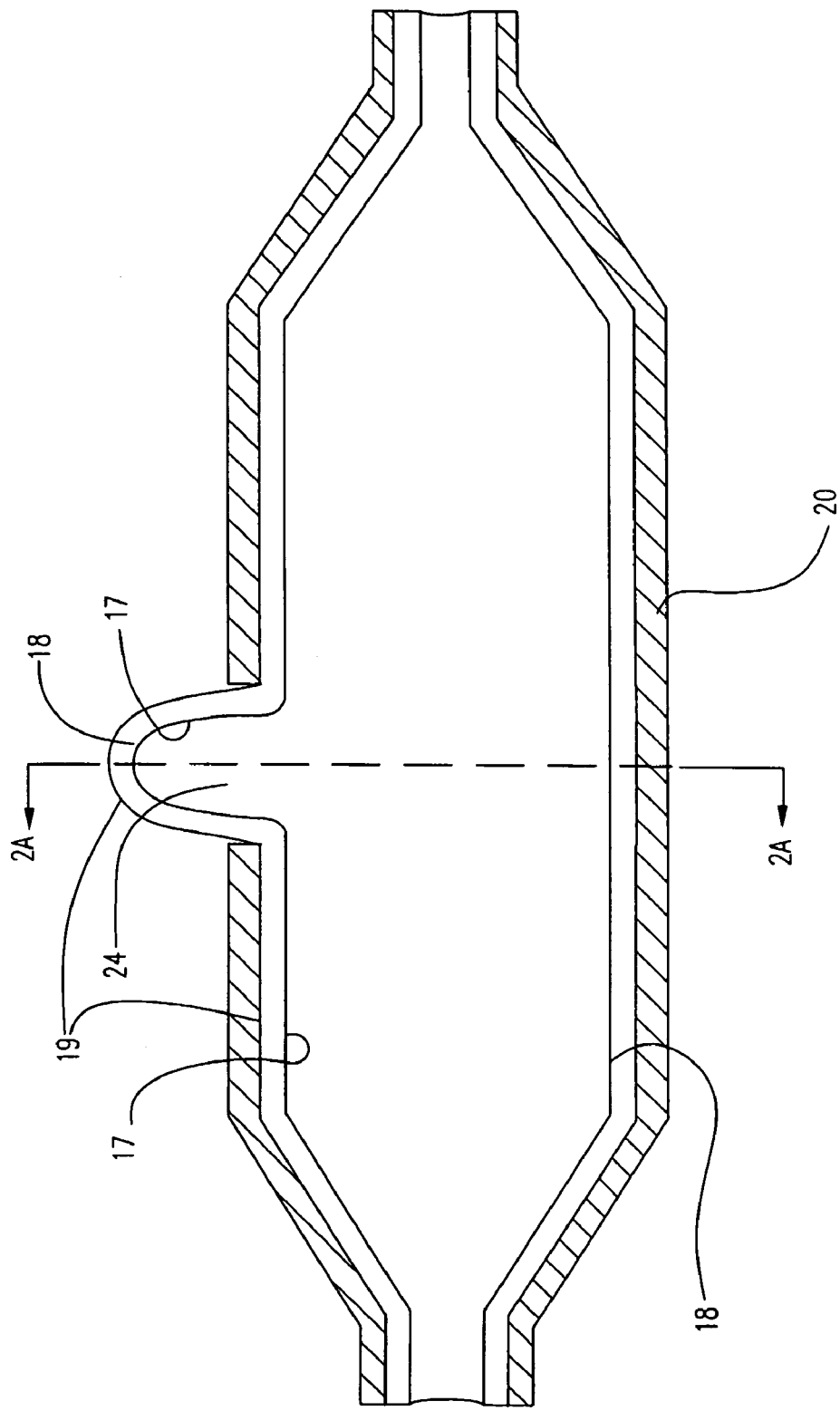

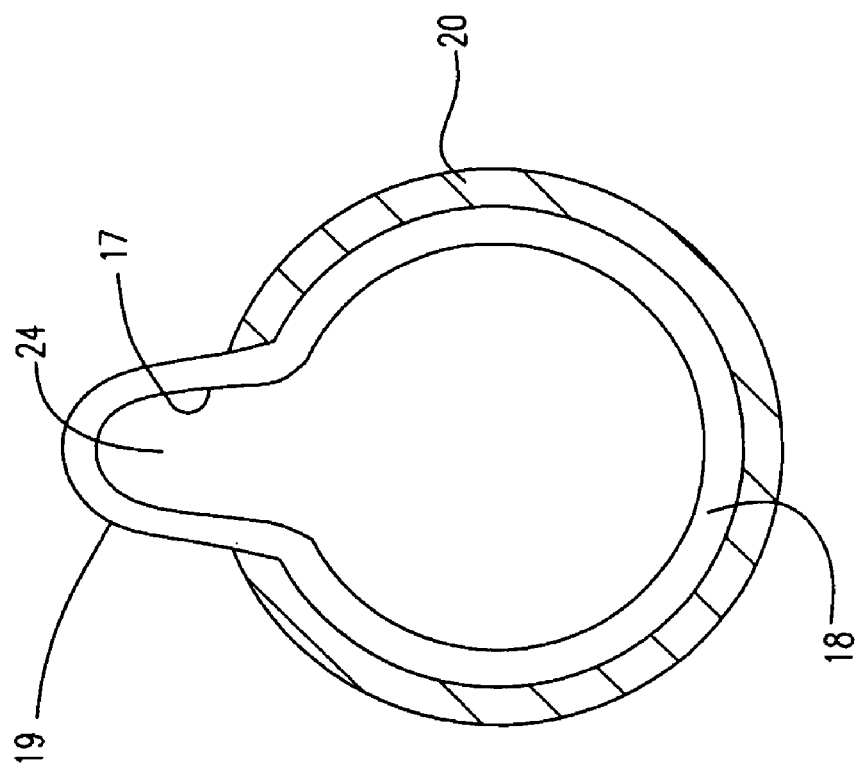

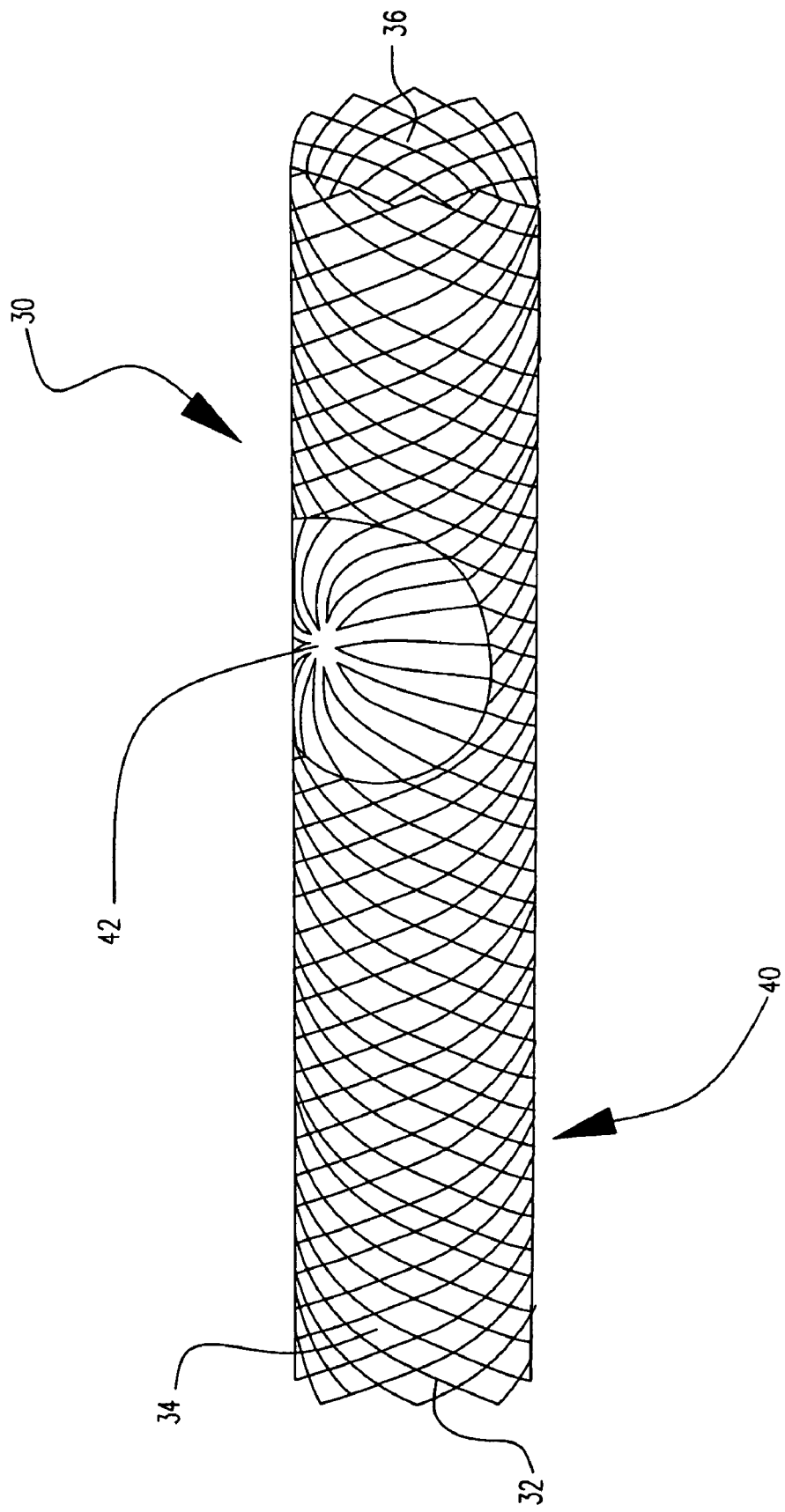

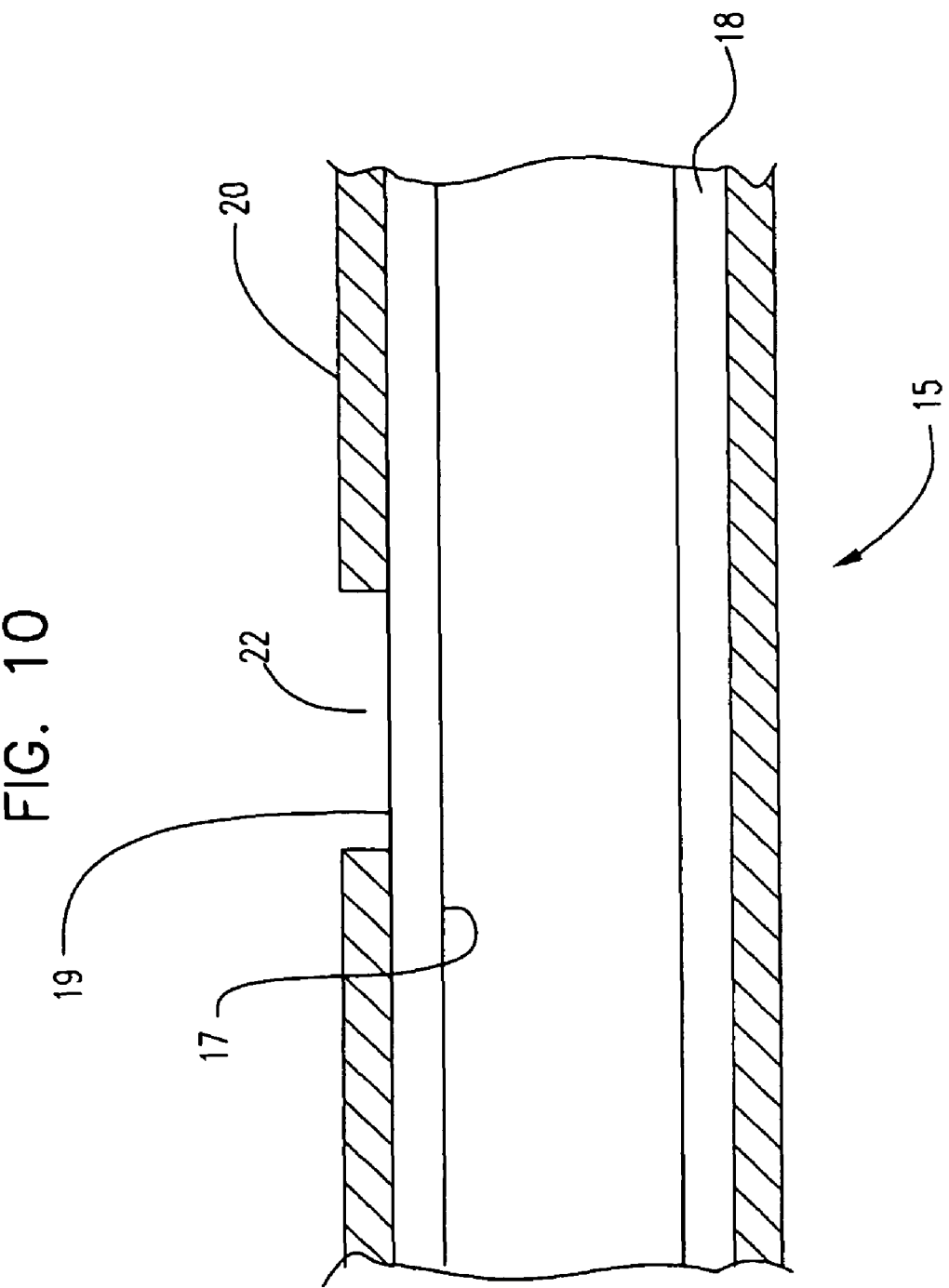

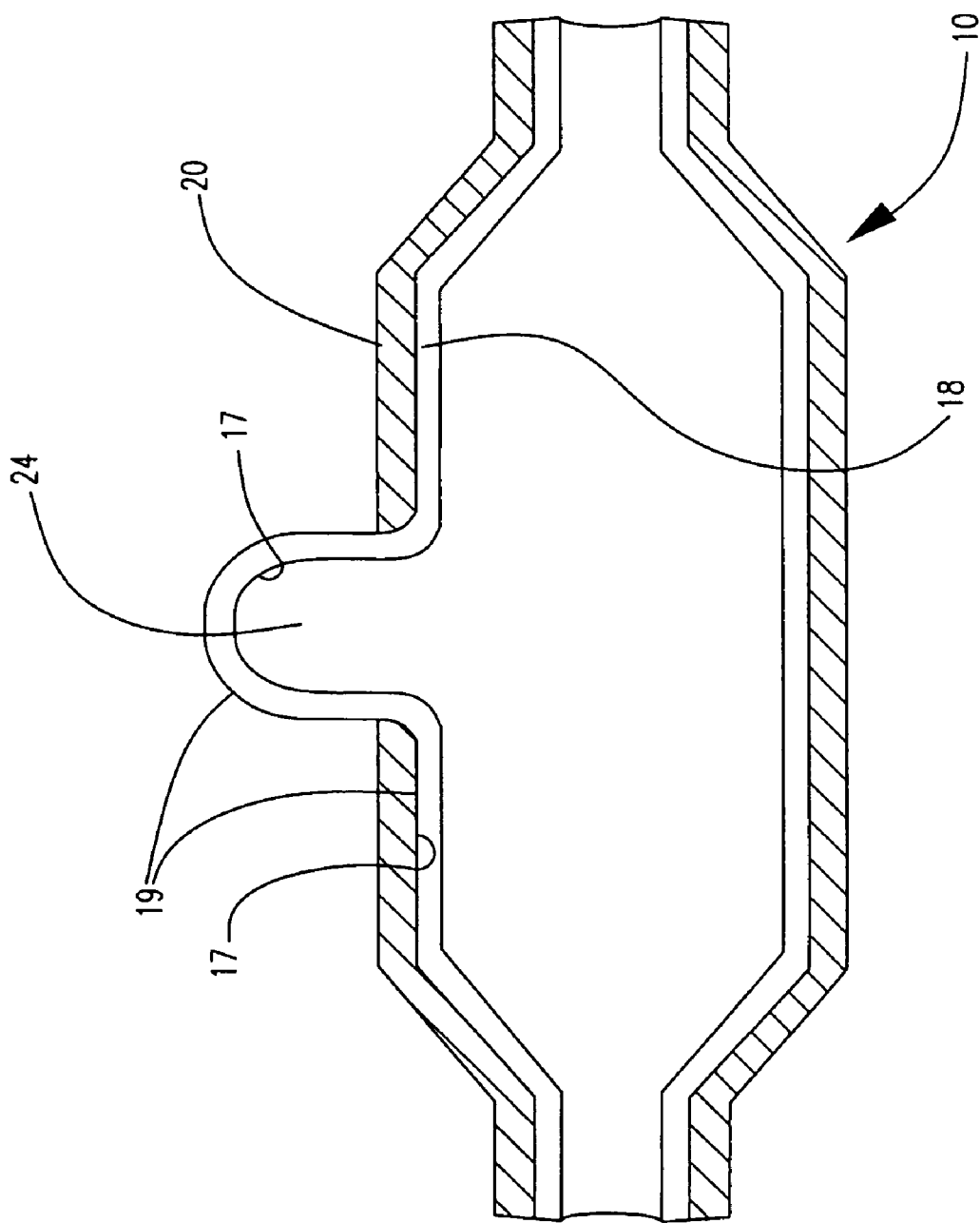

MULTILAYER BALLOON FOR BIFURCATED STENT DELIVERY AND METHODS OF MAKING AND USING THE SAME

FIELD OF THE INVENTION

The present invention relates to the field of expandable balloon members, particularly those for delivery of medical devices, particularly those delivered at or near a bifurcation of a body lumen.

BACKGROUND OF THE INVENTION

Vascular disease is prevalent and often involves the development of a stenosis within a body vessel which causes narrowing of the vessel, or which can lead to complete blockage (or occlusion), which leads to restriction or cessation of blood flow through this vessel.

Within the vasculature, it is not uncommon for a stenosis to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels.

Implantable medical devices, such as stents, are well known, and may be designed for treatment at vessel bifurcations. Stents are implantable devices which are introduced percutaneously, delivered transluminally to the treatment site in a reduced diameter profile, and once in position, are radially expanded to an enlarged diameter. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

A stent is typically delivered using a stent delivery device, such as a stent delivery catheter. In one common technique, the stent is crimped down to its delivery position over an expandable member, which is disposed at the distal end of the delivery catheter. The delivery catheter, with the expandable element and the stent disposed thereon, is advanced to the treatment site, wherein the balloon and the catheter are expanded, the expandable member deflated and withdrawn, leaving the stent deployed at the site.

Stents for use at vessel bifurcations may have a variety of configurations including, for example, segmented structures which include a primary branch and at least one secondary branch which is positioned adjacent to and/or partially within the primary branch. These segmented systems may employ multiple catheters and/or balloons to deploy all of the stent segments.

Other bifurcated stents include single structure stents wherein the stent is comprised of a trunk with two or more branches extending therefrom.

Still other stent configurations employ a single substantially tubular stent which has a specialized side-branch opening through which an additional stent or structural component may be deployed. Many of these systems employ a stent delivery assembly having a dual-balloon system for deployment of the main and the side-branch of the bifurcation stent.

In any case, it is desirable also to have delivery systems and components thereof, including the expandable members, to be configured for efficient and accurate deployment of these such stents at vessel bifurcations.

There remains a need in the art for improved delivery systems and components thereof, for delivery of stents at vessel bifurcations.

The information described above is not intended to constitute an admission that such information referred to herein is "prior art" with respect to this invention.

Without limiting the scope of the invention a brief summary of some of the claimed embodiments of the invention is set forth below. Additional details of the summarized embodiments of the invention and/or additional embodiments of the invention may be found in the Detailed Description of the Invention below.

SUMMARY OF THE INVENTION

The present invention relates to expandable medical balloons useful for delivery of implantable medical devices at vessel bifurcations.

In particular, the present invention relates to a single expandable medical balloon which is configured so as to allow for deployment of a bifurcation stent which has both main and side-branch openings.

In one aspect, the present invention relates to an expandable medical balloon useful for treatment of a bifurcated vessel, the balloon having at least one expanded state, the balloon formed with at least one inner layer and at least one outer layer, the outer layer having at least one cavity wherein the cavity extends at least partially through the outer layer and allows protrusion of the inner layer therethrough when the balloon is in its at least one expanded state. In one embodiment, the cavity extends completely through the outer layer thereby forming an opening through which the inner layer is exposed. The cavity is suitably located in the balloon body.

More specifically, the balloon is formed having at least one inner layer and at least one outer layer, wherein the outer layer has at least one protrusion region, the outer layer of the protrusion region having at least a partial thickness.

In one embodiment, the balloon is employed for the delivery of a bifurcated stent having a main branch and a side branch, wherein the inner layer protrusion corresponds with and extends into, the side branch of the bifurcated stent for expansion of the side branch.

Using a single multilayer balloon according to the invention allows for a more simplistic approach to stent delivery at vessel bifurcations than use of a dual-balloon system, for example.

These and other aspects, embodiments and advantages of the present invention will become immediately apparent to those of ordinary skill in the art upon review of the Detailed Description and Claims to follow.

BRIEF DESCRIPTION OF THE DRAWINGS

FIG. 1 is a longitudinal cross-section of an embodiment of a balloon in an unexpanded or static state in accordance with the invention.

FIG. 1A is a radial cross-section taken at section 1A-1A in FIG. 1.

FIG. 2 is a longitudinal cross-section of a balloon similar to that shown in FIGS. 1 and 1A in an expanded state.

FIG. 2A is a radial cross-section taken at section 2A-2A in FIG. 2.

FIG. 3 is a perspective view of a generic stent having a main and a side-branch opening for use at a vessel bifurcation.

FIG. 10 is a partial longitudinal cross-section of a portion of a multilayer balloon body after removal of material from the outer layer of a balloon preform similar to that in FIG. 9.

FIG. 11 is a longitudinal cross-section of an expandable balloon member formed as in FIGS. 9-10 in an expanded state.

DETAILED DESCRIPTION OF THE INVENTION

Figure 4:
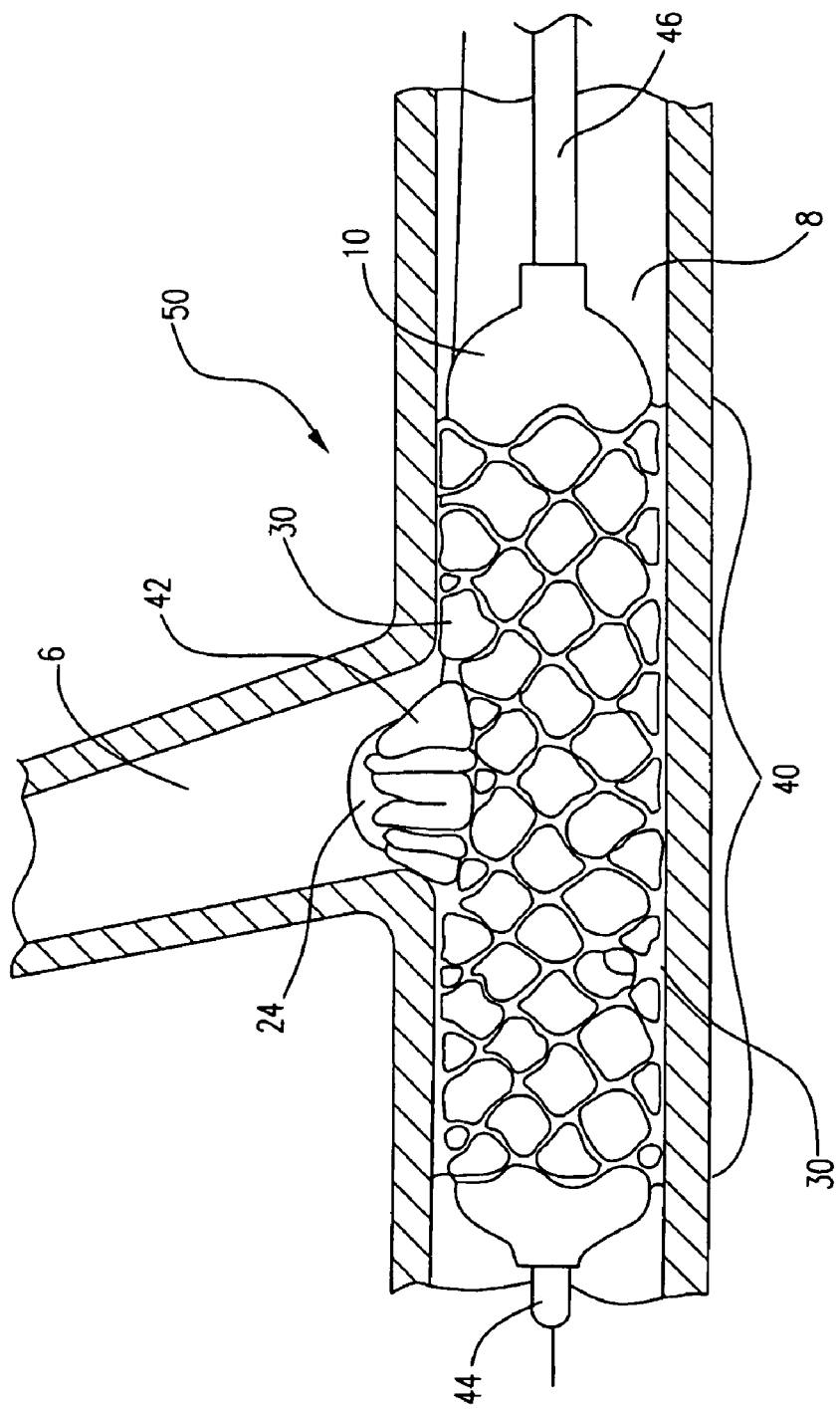
FIG. 4 is a side view of a stent similar to that shown in FIG. 3 disposed about an embodiment of a balloon according to the invention, each in their expanded configuration in an environment of use.
Figure 5:
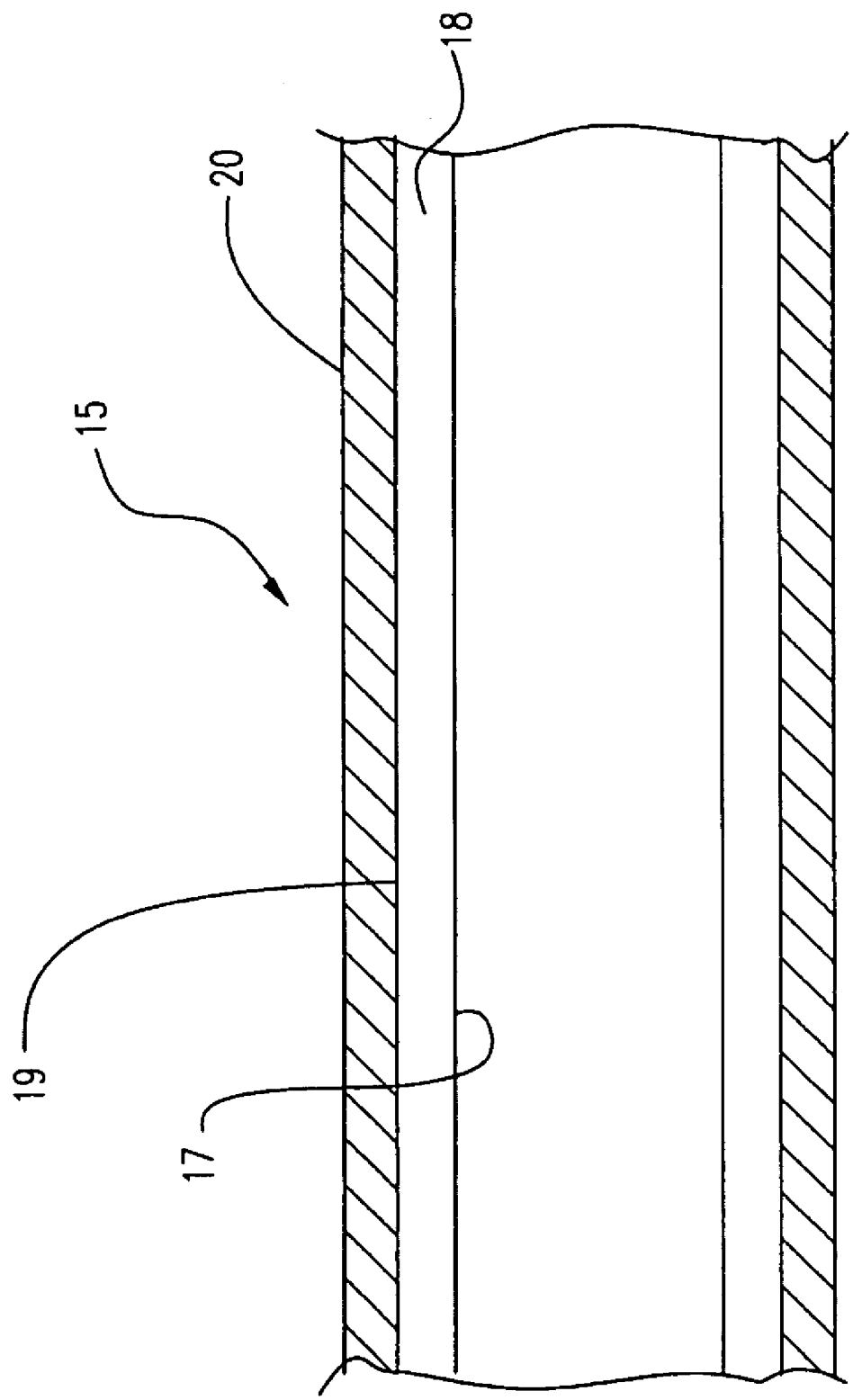
FIG. 5 is a partial longitudinal cross-section of a multilayer preform for a balloon.

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The present invention relates to a multilayer expandable medical balloon which finds particular utility for use in treatment of vessel bifurcations and for delivery of stents for treatment at a vessel bifurcation.

The balloon includes at least one inner layer and at least one outer layer, the outer layer having a cavity extending at least partially therethrough. The cavity may extend all the way through the outer layer forming an opening through which the outer surface of the inner layer is exposed. In one embodiment, the cavity extends completely through the outer layer thereby forming an opening through which the inner layer is exposed. The cavity allows the inner layer to expand therethrough.

More specifically, the balloon is formed having at least one inner layer and at least one outer layer, wherein the outer layer has at least one protrusion region, the outer layer of the protrusion region having at least a partial thickness.

The expandable balloons according to the invention find particular utility for delivery of an implantable medical device such as a stent having a main and a side-branch for use at a vessel bifurcation, wherein the balloon is employed to expand the stent from its unexpanded configuration to its expanded configuration during deployment.

The main branch of the stent may be positioned in the main branch of the vessel bifurcation. The side-branch of the stent may be positioned at the secondary or side-branch of the vessel bifurcation.

During delivery and deployment of the stent at the vessel bifurcation, the stent may be positioned over the balloon so that the side-branch opening of the stent is positioned over the cavity in the outer layer of the balloon. During expansion, the at least one inner layer of the multi-layer balloon expands into the cavity of the at least one outer layer, and protrudes therethrough, thereby expanding the side-branch of the stent into the ostium of the secondary vessel of the vessel bifurcation.

Depicted in the following figures are various aspects of the invention. Elements depicted in one figure may be combined with, and/or substituted for, elements depicted in another figure as desired.

Turning now to the figures, FIG. 1 is a longitudinal cross-section of a balloon 10 in an unexpanded or static state in accordance with the invention. As used herein, the term "static" shall be used to refer to the balloon as it is formed, prior to either deflation or expansion. For example, for a molded balloon, the static state is the state of the balloon as it is removed from the balloon mold. In FIG. 1, balloon 10 is shown having waist portions 12, cone portions 14 and body portion 16. Balloon is of a multilayer construction having at least one inner layer 18 and at least one outer layer 20. The inner layer has an inner surface 17 and an outer surface 19. Outer layer 20 has a cut-out region or cavity 22 extending therethrough such that the outer surface 19 of the inner layer 18 is exposed in the region. This region may also be referred to herein as a "protrusion" region. The cut-out region or cavity 22 of the outer layer 20 may also be of a partial thickness. While balloon 10 is shown in this embodiment having two layers, it should be noted that balloon 10 is not limited to two layers and can have any number of layers. FIG. 1A is a radial cross-section taken at section 1A-1A in FIG. 1.

FIG. 2 is a longitudinal cross-section of a balloon 10 similar to that shown in FIGS. 1 and 1A in an expanded state. In the expanded state, the inner layer 18 is shown with a protrusion 24 extending through cavity 22 (shown in FIGS. 1 and 1A). FIG. 2A is a radial cross-section taken at section 2A-2A in FIG. 2.

While the protrusion in FIG. 2 is shown having a generally half-circular or elliptical shape, it may take on other geometries as well if so desired.

Balloon 10 shown in FIGS. 1, 1A, 2 and 2A find particular utility for delivery of a stent having a main and a side-branch opening which can be employed at vessel bifurcations.

One embodiment of a generic stent configuration for deployment at a vessel bifurcation, shown for illustrative purposes only, is shown perspectively in FIG. 3. Stent 30 may be formed of wire or metal mesh wrapped into a cylindrical shape, or may be formed from a tubular member with strut patterns cut therein, or may be formed from a sheets of material which are wrapped or rolled into a cylindrical shape and the edges secured together using any suitable method known in the art. A stent pattern may be cut into the sheet before or after rolling. The present invention is not limited to any particular stent configuration. Stent 30 is shown having a primary or main stent body 40 which is formed of a plurality of interconnected stent members 32 which define a plurality of openings 34 which extend through the body 40, and which are in fluid communication with the primary lumen 36 of the stent body 40. Stent 30 is further configured with an opening 42 different from the other stent openings 34. Opening 42 is the side-branch opening of the stent. When the stent 30 is advanced to a vessel bifurcation, side-branch opening 42 will be aligned with the ostium of a secondary branch vessel adjacent the main vessel of a vessel bifurcation.

FIG. 4 is a side view of a stent mounted on the expandable balloon member 10 shown disposed about the distal end of an inner catheter shaft 44 and the distal end of an outer catheter shaft 46 and is shown in a bifurcated vessel 50. Vessel 50 is shown having a side branch 6 and a main branch 8. Balloon 10 has an inner layer and an outer layer as shown in FIGS. 1, 1A, 2 and 2A. Outer layer has an cavity as shown in FIGS. 1, 1A, 2 and 2A which, in an expanded state, the inner layer expands therethrough forming a protrusion 24. The protrusion 24 can be used to expand the side branch 42 of stent 30 into side branch 6 of vessel 50. Main body 40 of stent 30 is shown expanded in main branch 8 of vessel 50.

Multilayer balloon 10 according to the invention may be made using any conventional balloon forming techniques known to those of skill in the art. One commonly employed method includes the basic steps of extruding a tubular parison or balloon preform, placing the tubular parison in a balloon mold, and expanding the tubular parison into the desired balloon configuration in the balloon mold. The main processing steps may include other steps therein such as stretching and radial orientation of the balloon material, for example, as well as annealing and heat setting, if desired. The tubular parison may be stretched prior to molding, for example, in a separate step. The stretching step may also be combined with the radial expansion step while the tubular parison is in the balloon mold. An example of a balloon forming process is disclosed in U.S. Pat. No. 4,490,421 which is incorporated by reference herein in its entirety. Other suitable methods are known in the art.

Figure 6:
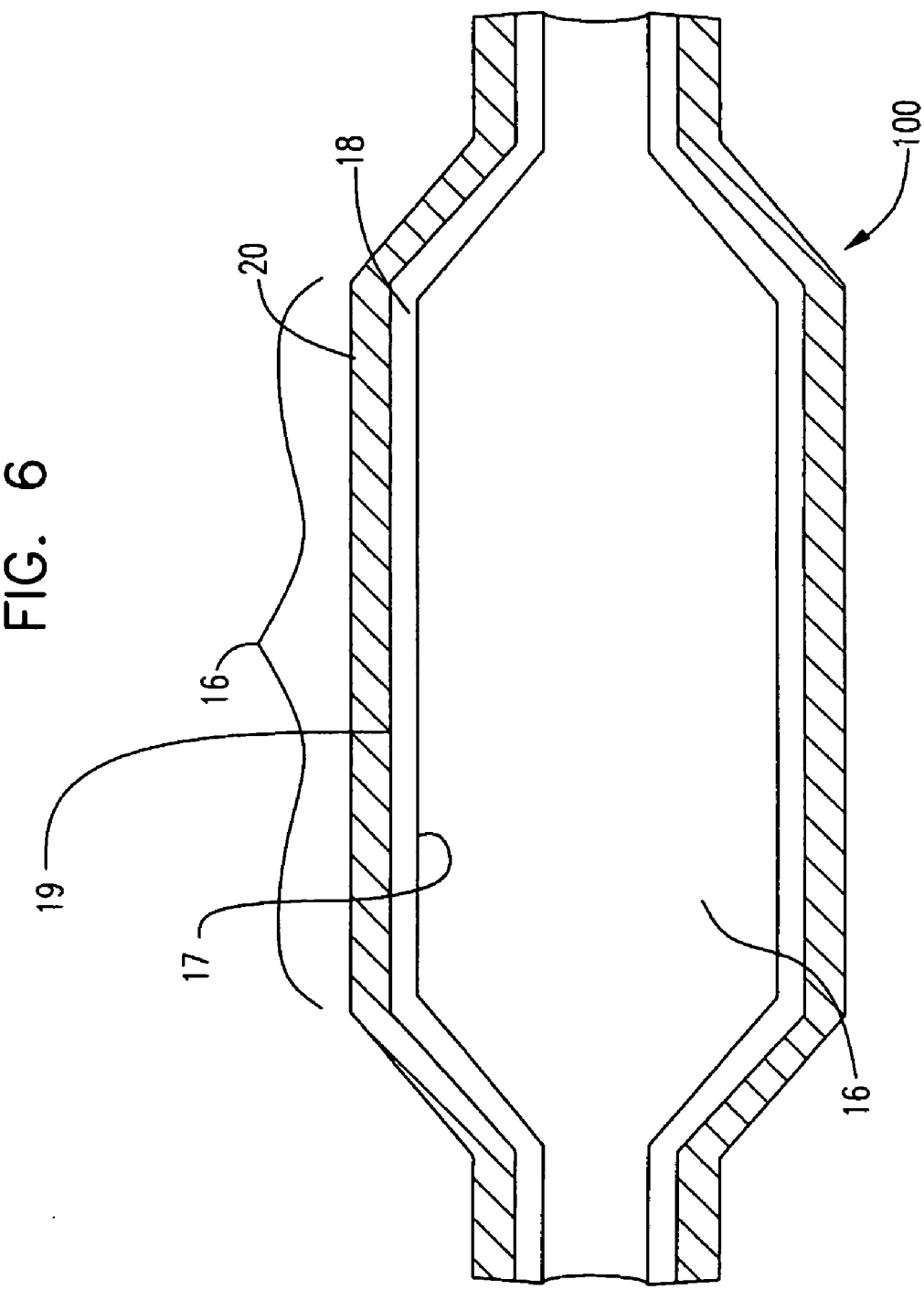
FIG. 6 is a longitudinal cross-section of a balloon formed from a multilayer preform similar to that in FIG. 5 in a static state.
Figure 7:
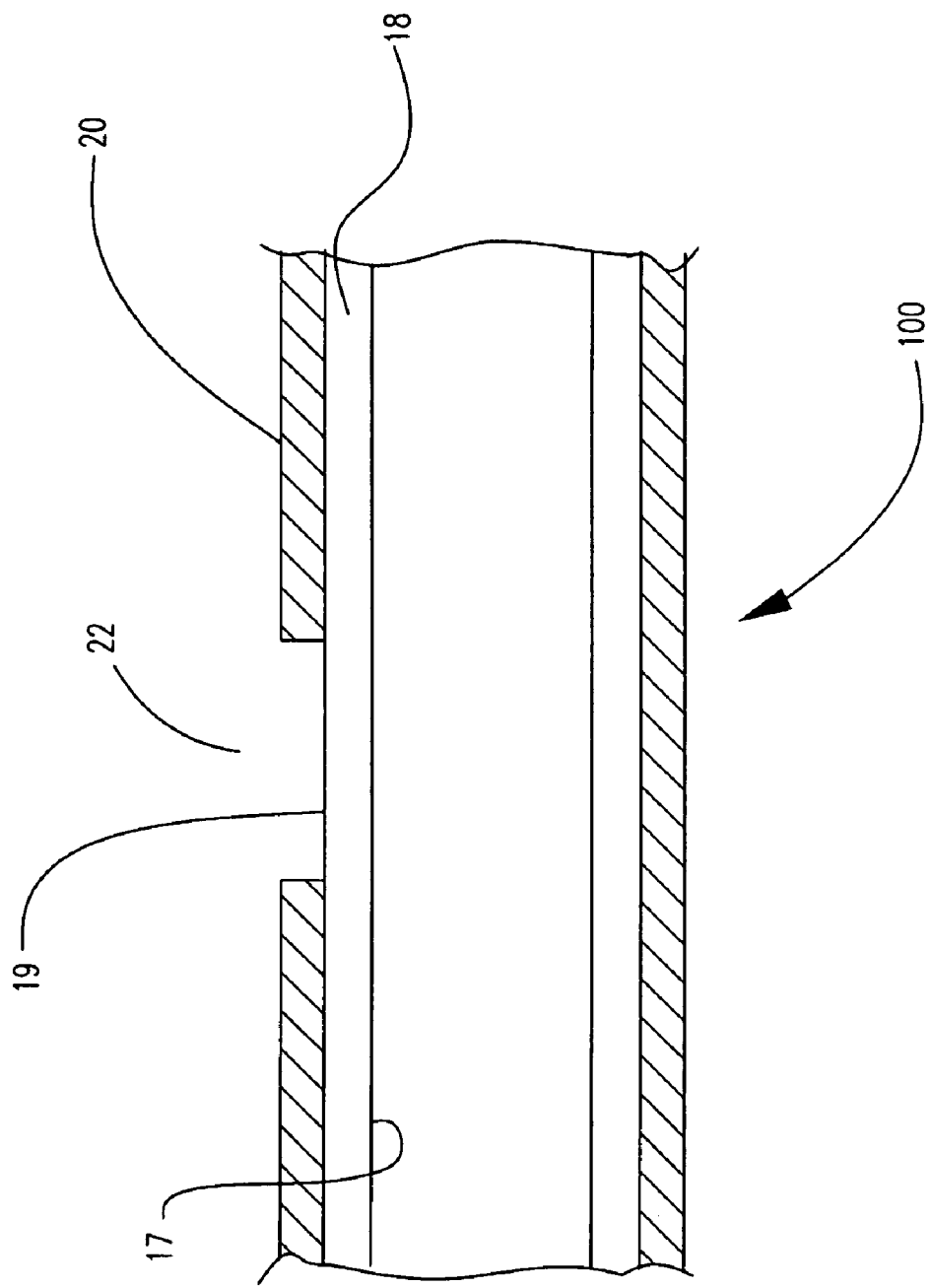
FIG. 7 is a partial longitudinal cross-section of a portion of a multilayer balloon body as in FIG. 6 after removal of material from the outer layer.

FIGS. 5-8 illustrate one embodiment of a method of making an expandable multilayer balloon. In a first step, a tubular multilayer balloon preform 15, as shown as a partial longitudinal cross-section in FIG. 5, may be formed as is known in the art such as by coextrusion. Balloon preform 15 has an inner layer 18 and an outer layer 20. The inner layer 18 has an inner surface 17 and an outer surface 19. The balloon preform 15 may then be placed in a balloon mold and radially expanded as is known in the art to form a balloon 100 as shown in FIG. 6. As balloon 100 is removed from the mold, it is considered to be in its static state. After this step, the outer layer 20 is continuous with the inner layer 18. In order to provide the cavity 22 in the outer layer 20 as shown as an expanded partial longitudinal cross-section of balloon body 16, material may be removed from the balloon 100 using any suitable technique such as by laser ablation, grinding, chemical etching, etc. wherein the cavity 22 in the outer layer is an opening extending therethrough with the outer surface 19 of the inner layer 18 of the balloon 100 exposed. As noted above, cavity 22 may also be of a partial thickness. Laser ablation methods are known and disclosed in, for example, commonly assigned U.S. Pat. No. 5,826,588 which is incorporated by reference herein in its entirety.

Figure 8:
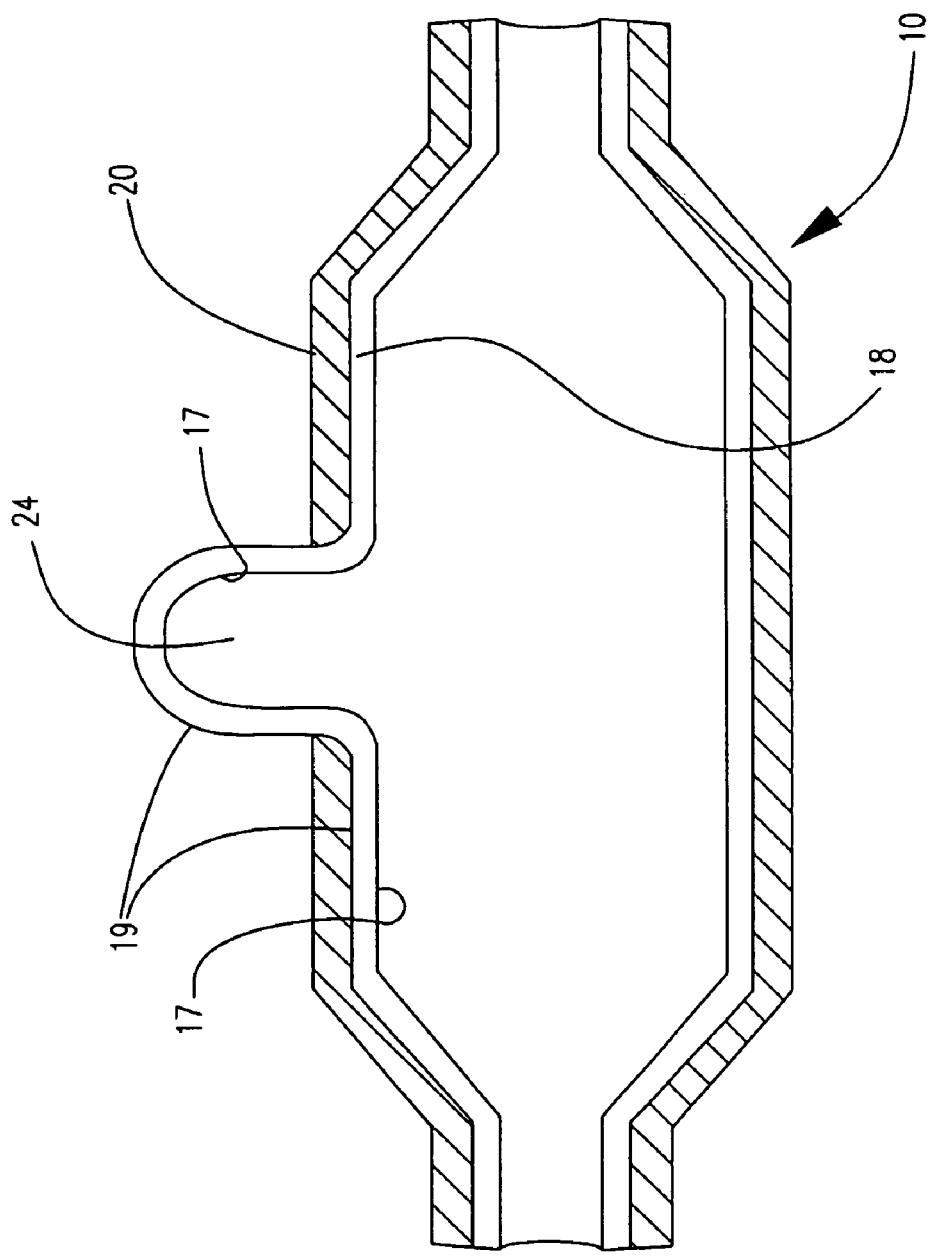
FIG. 8 is a longitudinal cross-section of an expandable balloon member formed as in FIGS. 5-7 in an expanded state.

A second forming processing may be employed to create the final balloon 10 shown as a partial longitudinal cross-section in FIG. 8 by placing balloon 100 in a mold and radially expanding to form the final balloon 10 as shown in FIG. 8. The balloon 10 is removed from the mold in its static state, i.e. prior to expansion or deflation. The cavity (not shown) allows the inner layer 18 to expand outwardly into a bulge 24. This can be advantageously employed to expand a side-branch of a bifurcated stent as explained above.

However, the second forming process may not be necessary as protrusion of the inner layer may occur when the balloon is pressurized.

Figure 9:
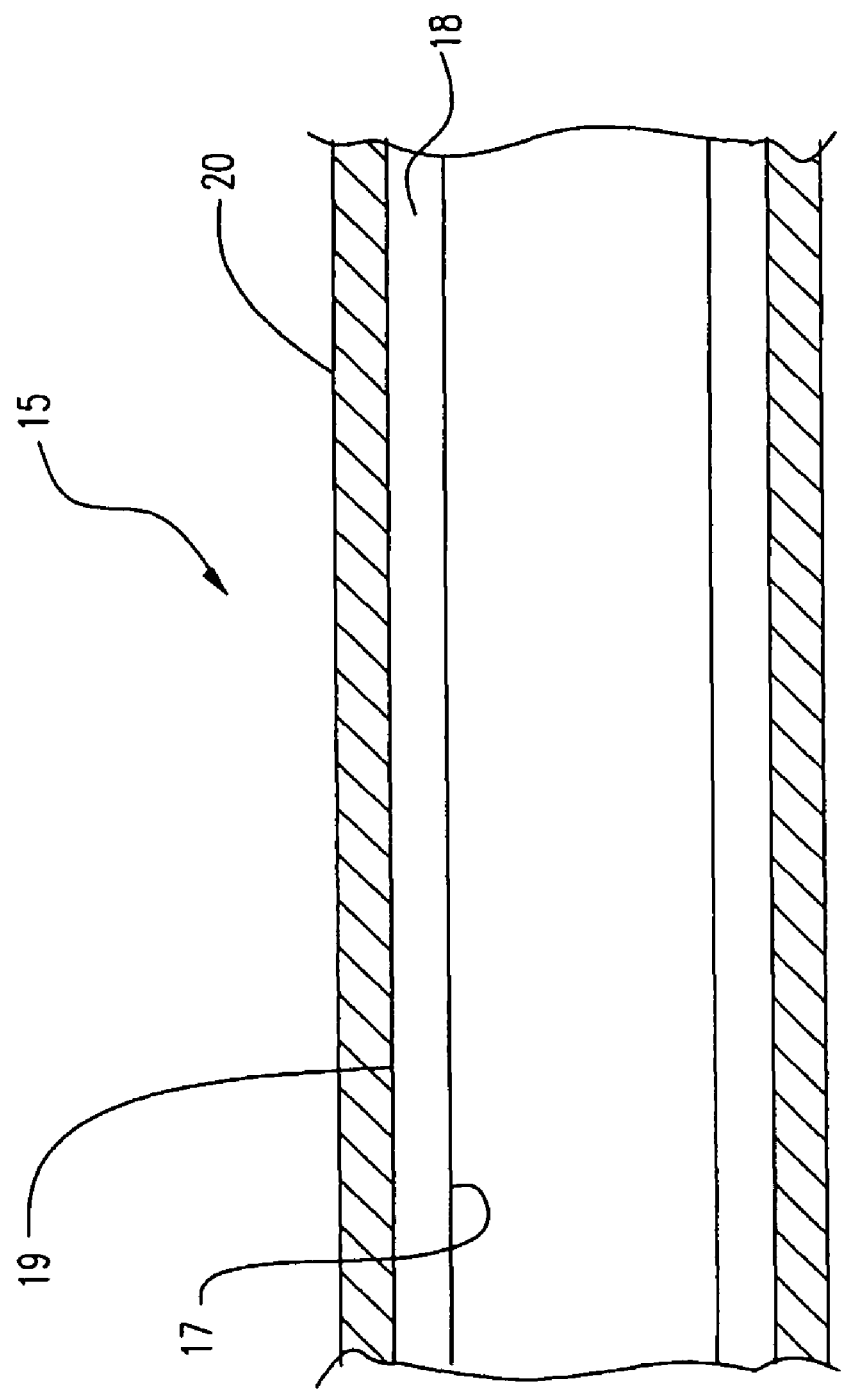
FIG. 9 is a partial longitudinal cross-section of a multilayer preform for a balloon.

In an alternative process as shown in FIGS. 9-11, the multilayer tubular parison 15 is formed using any suitable technique as described above such as by coextrusion. A partial longitudinal cross-section of multilayer tubular parison 15 having an inner layer 18 and an outer layer 20 is shown in FIG. 9. The inner layer 18 has an inner surface 17 and an outer surface 19. The tubular parison may first be formed using any method known in the art such as coextrusion of the layered parison, or tube-in-tube methods wherein tubes are first formed, and then inserted one in another. Using such methods, material may then be removed from the tubular parison 15 leaving a cavity 22 in the outer layer 20 which is of a partial thickness, or which extends all the way through the outer layer and forming an opening through which the outer surface of the inner layer is exposed. Removal of material may be accomplished using any suitable technique such as by laser ablation, chemical etching, grinding, etc. as is known in the art.

Another suitable method which can be employed is intermittent layer coextrusion (ILC) wherein the opening(s) is provided in the outer layer 20 during coextrusion.

Tubular parison 15 may then be placed into a balloon mold, and radially expanded resulting in balloon 10 as shown in FIG. 11.

After any of the molding steps, a heat set step may be employed if desired.

Once formed, the balloon may be folded and wrapped about its longitudinal axis as is known in the art.

It should be noted herein that the geometry of the protrusion can be changed by changing the geometry within the balloon mold.

Furthermore, if so desired, the process above can be modified so as to provide two or more cavities in the outer layer and two or more protrusions into the cavities from the inner layer.

Alternatively, the layers may be formed using other methods known in the art. For example, the tubular parison may be formed of a single layer, and subsequent layers may be applied using other techniques such as by chemical treatment, polymerization of an outer layer on the first, ion bombardment, etc.

A single layer balloon may also be formed followed by chemical treatment, polymerization of an outer layer, ion bombardment, etc.

Any suitable balloon material may be employed for the inner layer and the outer layer. Suitably, the outer layer is formed from a material which is different than that of the inner layer. Suitably, the at least one inner layer is made from a material which has a different compliance than that of the outer layer, i.e. is either more compliant or less compliant than the outer layer.

Suitably, the material for the outer layer is selected so as to be of the compliance desired for deployment of a stent in a main branch vessel. Examples of suitable balloon materials for the outer layer, for example, include, but are not limited to, polyolefins such as polyethylene, polyesters such as polyethylene terephthalate (PET) and polybutylene terephthalate (PBT), and polyamides (nylons), for example, are commonly employed for deployment of a stent in a main branch vessel.

Materials which may form compliant or semi-compliant balloon layers are those which are relatively soft or flexible polymeric materials. Examples of these materials include, but are not limited to, polyethylene (high density, low density, intermediate density, linear low density), various copolymers and blends of polyethylene, ionomers, polyesters, polyurethanes, polycarbonates, polyamides, polyvinyl chloride, acrylonitrile-butadiene-styrene copolymers, polyether-polyester copolymers, polyether-polyamide copolymers, block copolymers having styrene endblocks and midblocks of isoprene, butadiene, ethylene/propylene, isobutylene and ethylene/butylene, PTFE (TEFLON®), polyester-ester elastomers, polyether-ester elastomers such as HYTREL® and ARNITEL®, polyether-ether ketone (PEEK), polyetherblock amides (PEBAX®) and mixtures thereof.

It has been suggested that intermediate compliance balloons may be made polymers such as polyethylene ionomer, polyvinyl chloride, polyethylene or ethylene-vinyl acetate, nylon, polyether-block amides, and styrenic block copolymers, for example, as well as mixtures thereof.

Materials which may form relatively non-compliant balloon layers may be formed from relatively rigid or stiff polymeric materials. These materials include thermoplastic polymers and thermoset polymeric materials. Some examples of such materials include, but are not limited to, the polyalkylene terephthalates such as polyethylene terephthalate (PET) and polybutylene terephthalate (PBT), polyimides, thermoplastic polyimides, polyamides, polyesters, polycarbonates, polyphenylene sulfides, polypropylene, rigid polyurethanes as well as mixtures thereof.

As can be seen, some classes of materials, such as polyethylene or polyamides, for example, have members which fall into one or more of the compliance categories, depending on their chemical composition, chemical structure and processing parameters to which they are subjected, for example.

For a discussion of compliance, see, for example, commonly assigned U.S. Pat. Nos. 6,171,278, 6,146,356, 5,951,941, 5,830,182, 5,556,383 and 5,447,497, each of which is incorporated by reference herein in its entirety.

Non-limiting examples of balloon materials may be found in commonly assigned U.S. Pat. Nos. 5,500,181, 5,403,340 and 5,348,538, each of which is incorporated by reference herein in its entirety.

Of course, either layer may include reinforcement materials. Examples include fiber or filament forms such as polyester, polyamide or carbon fiber, and further may be sphere and particulate forms such as glass. Examples of reinforcing materials include, but are not limited to, glass, carbon, ceramic, fluoropolymer, graphite, liquid crystal polymers, polyester, polyamide, stainless steel, titanium and other metals such as nitinol, or radiopaque materials (such as Bismuth or Tungsten) and the like. Reinforcement materials are disclosed in commonly assigned U.S. Pat. No. 6,024,722, the entire content of which is incorporated by reference herein.

Nanocomposite or microcomposite materials may be employed herein. "Nanocomposite" or "microcomposite" are terms art often used to refer to compositions that include a polymeric material and relatively small amounts (generally less than about 10% by weight) of nanometer-sized (average size smaller than 1 micrometer) mineral clay or nanosized ceramic particles dispersed therein, for example. Sometimes nanocomposites are referred to as "nanoclay" or "nanoceramic". For example, nanocomposites are disclosed in commonly assigned copending WO 03/049795 A2, the entire content of which is incorporated by reference herein. See also WO 930004118, commonly assigned U.S. Patent Application No. 20050149177, and U.S. Pat. Nos. 5,385,776, and 6,251,980, each of which is incorporated by reference herein in its entirety.

These materials can be added for the purpose of restricting or controlling compliance. Radiopaque materials may be added to provide a visual aid for positioning of the balloon and/or stent at the treatment site in a body lumen, for example.

The above lists are intended for illustrative purposes only, and not as a limitation on the scope of the present invention.

The expandable balloon members according to the invention find utility in the treatment of vascular disease, particularly for the treatment of disease at vessel bifurcations. Procedures wherein such balloons may be employed include, for example, plain old balloon angioplasty (POBA) and percutaneous transluminal coronary angioplasty (PTCA), as well as delivery of implantable medical devices such as stent delivery.

The multilayer expandable balloon members as disclosed herein allow for delivery of stents at vessel bifurcations using a single balloon member. The use of a single balloon member is advantageous for a variety of reasons including easier, more efficient assembly, easier balloon folding/wrapping and crimping of the stents onto the balloon and reduced withdrawal force post-stent deployment.

The multilayer expandable balloon members can be employed in combination with any catheter assembly used for vascular treatment and in combination with any stent delivery device employed in such treatments.

The following non-limiting example is further illustrative of the present invention.

EXAMPLES

Example 1

A tubular parison having an inner layer of PEBAX® 6333, poly(ether-block-amide), available from Arkema Inc. in Philadelphia, Pa., and an outer layer of Melinar Laser+® polyethylene terephthalate (PET), available from Advansa in Hoofddorp, The Netherlands, was coextruded. The inner diameter of the coextruded tubular parison was 0.023" and the outer diameter of 0.046". The inner layer and outer layer were extruded at equal mass flow rates. The extruder was employed with several heating zones ranging from about 350° F. (about 177° C.) to about 515° F. (about 268° C.). A balloon was formed by placing the tubular parison in a conventional balloon mold form such as disclosed in commonly assigned U.S. Pat. No. 5,714,110 to Wang (see FIG. 4), the entire content of which is incorporated by reference, and radially expanding the tubular parison into the mold form at a temperature of 95° C. and 350 psi (about 2.40 megapascal). The balloon dimensions were 3.0 mm×24.0 mm. After radial expansion in the balloon mold, the thickness of the outer layer is slightly less than the thickness of the inner layer.

Once the balloon was formed, a substantially circular section having a diameter of about 1.5 mm was cut into the outer layer of the balloon with a UV laser, forming an opening extending all the way through the outer layer, exposing the outer surface of the inner layer.

Upon inflation to a pressure of about 10 atm, the main branch portion of the balloon was expanded. After inflation to 15 atm, the inner layer expanded through the opening to form a protrusion, i.e. the size branch portion of the balloon.

It should be noted that inflation pressures may vary depending on the materials selected, processing parameters, and balloon wall thickness.

Other factors which may affect side branch deployment include the shape and dimensions of the cavity and the thickness of the outer layer in the cavity region.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. An expandable medical balloon useful for treatment of a bifurcated vessel, the balloon comprising a body, waist and cone portions, the balloon body having a central body portion, the balloon having an unexpanded and at least one expanded state, in the unexpanded state the balloon comprising at least one continuous inner layer, the inner layer having an inner surface and an outer surface, and at least one outer layer, the outer layer is integral with the inner layer and in the body portion is coextensive therewith except for a cavity in the central portion of the balloon body, said cavity is a single opening which extends through the outer layer exposing the outer surface of the inner layer, the at least one inner layer protruding through the cavity in the at least one outer layer when the balloon is in said at least one expanded state, the balloon comprising the inner layer and the outer layer in the unexpanded and expanded states.

2. The expandable medical balloon of claim 1 wherein the at least one outer layer is formed of a material wherein said outer layer is of a first compliance, and the inner layer is formed of a material wherein said inner layer of a second compliance, the second compliance is less than the first compliance.

3. The expandable medical balloon of claim 1 wherein the at least one outer layer is formed of a material wherein said outer layer is of a first compliance, and the inner layer is formed of a material wherein the inner layer is of a second compliance, the second compliance is greater than the first compliance.

4. The expandable medical balloon of claim 1 wherein the at least one outer layer is formed from at least one material selected from the group consisting of homopolymers, copolymers and terpolymers of ethylene, polyamides, polyalkylene terephthalates, polyimides, polyesters, copolyesters, polycarbonates, polyphenylene sulfides, polypropylene, polyurethanes and mixtures thereof.

5. The expandable medical balloon of claim 1 wherein said inner layer is selected from the group consisting of homopolymers, copolymers and terpolymers of ethylene, polyesters, copolyesters, polyurethanes, polycarbonates, polyamides, polyvinyl chloride, acrylonitrile-butadiene-styrene copolymers, polyether-polyester copolymers, polyether-polyamide copolymers, block copolymers having styrene endblocks and midblocks of isoprene, butadiene, ethylene/propylene, isobutylene and ethylene/butylene, fluoropolymers, polyester-ester elastomers, polyether-ester elastomers, polyether-ether ketone, polyether-block amides and mixtures thereof.

6. The expandable medical balloon of claim 1 in combination with a bifurcated stent, the bifurcated stent having a main branch and a side-branch and having an expanded state, and wherein the side-branch of the stent corresponds to the cavity through which the inner layer protrudes, and in the expanded state, the inner layer of the expandable medical balloon protrudes into the side-branch opening of the stent.

7. The expandable medical balloon of claim 1 in combination with a stent delivery catheter.

8. The expandable medical balloon of claim 1 wherein said balloon comprises at least a portion of a stent delivery catheter.

* * * * *